(12) United States Patent
Jaehne et al.

(10) Patent No.: US 7,081,467 B2
(45) Date of Patent: Jul. 25, 2006

(54) C2-DISUBSTITUTED INDAN-1-ONES AND THEIR DERIVATIVES, PROCESSES FOR THEIR PREPARATION AND THEIR USE AS PHARMACEUTICALS

(75) Inventors: Gerhard Jaehne, Frankfurt (DE); Volker Krone, Hofheim (DE); Martin Bickel, Bad Homburg (DE); Matthias Gossel, Hofheim (DE)

(73) Assignee: Sanofi-aventis Deutschland GmbH, Frankfurt (DE)

( * ) Notice: Subject to any disclaimer, the term of this patent is extended or adjusted under 35 U.S.C. 154(b) by 238 days.

(21) Appl. No.: 10/230,464

(22) Filed: Aug. 29, 2002

(65) Prior Publication Data

US 2003/0153609 A1 Aug. 14, 2003

(30) Foreign Application Priority Data

Aug. 31, 2001 (DE) ............... 101 42 665

(51) Int. Cl.
| | | |
|---|---|---|
| A61K 31/10 | (2006.01) | |
| A61K 31/41 | (2006.01) | |
| A61K 31/42 | (2006.01) | |
| A61K 31/4418 | (2006.01) | |
| A61K 31/4192 | (2006.01) | |
| A61K 31/425 | (2006.01) | |
| C07C 317/12 | (2006.01) | |
| C07D 213/24 | (2006.01) | |

(52) U.S. Cl. .............. 514/336; 514/365; 514/374; 514/381; 514/383; 514/396; 514/438; 514/461; 514/706; 514/708; 546/268.1; 548/146; 548/215; 548/250; 548/262.2; 548/300.1; 549/29; 549/429; 568/18; 568/20

(58) Field of Classification Search ............ 548/215, 548/250, 300.1, 262.2, 146; 549/29, 429; 546/268.1; 514/336, 365, 374, 381, 383, 514/396, 438, 461, 706, 708; 568/18, 20
See application file for complete search history.

(56) References Cited

U.S. PATENT DOCUMENTS

| | | | |
|---|---|---|---|
| 4,063,950 A * | 12/1977 | Fujiwara et al. | 430/382 |
| 4,129,656 A | 12/1978 | Lang | |
| 4,174,397 A | 11/1979 | Knabe | |
| 5,232,940 A | 8/1993 | Hatton et al. | |
| 6,090,833 A | 7/2000 | Jaehne | |
| 6,159,996 A | 12/2000 | Jaehne | |
| 6,235,763 B1 | 5/2001 | Jaehne | |

FOREIGN PATENT DOCUMENTS

| | | |
|---|---|---|
| EP | 0234119 A | 9/1987 |
| EP | 0295117 A | 12/1988 |
| WO | 94/13643 A | 6/1994 |
| WO | WO 97/20806 | 6/1997 |
| WO | WO 97/26265 | 7/1997 |
| WO | 97/32843 A | 9/1997 |
| WO | WO 97/41097 | 11/1997 |
| WO | WO 98/08871 | 3/1998 |
| WO | 98/39302 A | 9/1998 |
| WO | WO 98/55439 | 12/1998 |
| WO | WO 99/03861 | 1/1999 |
| WO | WO 01/12176 | 2/2001 |

OTHER PUBLICATIONS

Russell et al, "Thermally cleavable safety-catch linkers for solid-phase chemistry." Tetrahedron Letters (2000), vol. 41, pp. 5287-5290.*
Russell et al, "Thermally cleavable safety-catch linkers for solid-phase chemistry." Tetrahedron Letters (2000), vol. 41, pp. 5287-5290.*
Copp, et al., Synthesis of 5,6,6a,7,7a,12a-Hexahydro-4H-benzo[d,e] benzothiano-[2,3-g] quinolines and 8-Phenyl-2,3,7,8,9,9a-hexahydro-1H-benzo[d,e] quinolines, J. Chem. Soc. Perkin Trans. I (1983), 909-914.

(Continued)

Primary Examiner—Joseph K. McKane
Assistant Examiner—Janet L Coppins
(74) Attorney, Agent, or Firm—Julie Anne Knight; Raymond S. Parker, III

(57) ABSTRACT

The present invention is directed C2-disubstituted indan-1-ones of the Formula I,

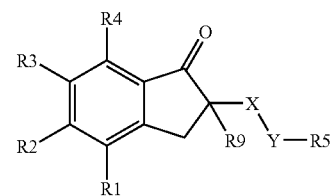

physiologically acceptable salts, and physiologically functional derivatives thereof, and pharmaceutical compositions comprising such compounds, salts and derivatives, which are useful for reducing weight, for the prophylaxis or treatment of obesity, and for the prophylaxis or treatment of type II diabetes in mammals. The invention is directed also to methods for reducing weight and such treatments and prophylaxis. The invention is directed also to processes for the preparation of such compounds.

5 Claims, No Drawings

OTHER PUBLICATIONS

Rote Liste 2001, ECV Editio Cantor Verlag.

Edwards, D. et al., The Oxidation Of Alkyl Sulphides, J. Chem. Soc., 1954, pp. 3272-3274.

Lambert, P. D. et al., Ciliary Neurotrophic Factor Activates Leptin-Like Pathways And Reduces Body Fat, Without Cachaxia Or Rebound Weight Gain, Even in Leptin-Resistant Obesity, PNAS, Apr. 10, 2001, vol. 98, No. 8, pp. 4652-4657.

Maiti, A. K. et al., Polyethylene Glycol (PEG) 4000 Catalysed Regioselective Nucleophilic Ring Opening Of Oxiranas—A New And Convenient Synthesis Of Beta-Hydroxy Sulfone And Beta-Hydroxy Sulfide, Tetrahedron vol. 50, No. 35, pp. 10483-10490, 1994.

Monteiro, Hugo J. et al., A New Synthesis Of Beta-Keto-Phenylsulfoxides, Tetrahedron Letters No. 11, pp. 921-924, 1975.

Seebach, Dieter et al., Hers tallung Alpha-Thioilerter Carbonylverbindungen, Chem. Ber. 109, 1601-1616, 1976.

Sviridova, V. I. Leba et al., A Method For The Selective Oxidation Of Sulfides To Sulfoxides, J. Org. Chem (Russ), 7, pp. 2577-2580 (1971).

Tyle, Praveen, Iontophoretic Devices For Drug Delivery, Pharmaceutical Research, vol. 3, No. 6, 1986.

Venier, Clifford G. et al., Petroxytrifluoroacetic Acid. A Convenient Reagent For The Preparation of Sulfoxides And Sulfones, J. Org. Chem. 1982, 47, 3773-3774.

* cited by examiner

C2-DISUBSTITUTED INDAN-1-ONES AND THEIR DERIVATIVES, PROCESSES FOR THEIR PREPARATION AND THEIR USE AS PHARMACEUTICALS

FIELD OF THE INVENTION

The invention relates to C2-disubstituted indan-1-ones and their derivatives and also their physiologically acceptable salts and physiologically functional derivatives.

BACKGROUND OF THE INVENTION

In F. C. Copp et al., J. Chem. Soc. Perkin I, 1983, 909–914, in the preparation of 2-phenylindan-1-one, 2-phenyl-2-phenylthioindan-1-one is obtained as an intermediate.

WO 97/20806 discloses cyclopentyl-substituted indan-1-one derivatives having inter alia antiinflammatory action.

WO 98/55439 discloses indan-1-one derivatives which are disubstituted at C2 and have antiinflammatory action.

SUMMARY OF THE INVENTION

It is an object of the present invention to provide compounds which cause a reduction in weight in mammals and which are suitable for preventing and treating obesity.

DETAILED DESCRIPTION OF THE INVENTION

Accordingly, the invention relates to compounds of the formula (I)

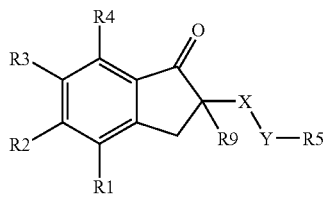

I in which

R1, R2, R3, R4 independently of one another are H, F, Cl, Br, I, CN; $N_3$, $NO_2$, OH, $O(C_1-C_8)$-alkyl, $O(C_3-C_8)$-cycloalkyl, $O-CH_2$-phenyl, O-phenyl, $O-CO-(C_1-C_8)$-alkyl, $O-CO-(C_3-C_8)$-cycloalkyl, $S(O)_{0-2}(C_1-C_8)$-alkyl, $S(O)_{0-2}(C_3-C_8)$-cycloalkyl, $NH_2$, $NH-(C_1-C_8)$-alkyl, $NH-(C_3-C_8)$-cycloalkyl, $N[(C_1-C_8)$-alkyl]$_2$, $N[(C_3-C_8)$-cycloalkyl]$_2$, $NH-CO-(C_1-C_8)$-alkyl, $NH-CO-(C_3-C_8)$-cycloalkyl; $SO_3H$, $SO_2-NH_2$, $SO2-NH-(C_1-C_8)$-alkyl, $SO_2-NH-(C_3-C_8)$-cycloalkyl, $NH-SO_2-NH_2$, $NH-SO_2-(C_1-C_8)$-alkyl, $NH-SO_2-(C_3-C_8)$-cycloalkyl, $O-CH_2-COOH$, $O-CH_2-CO-O(C_1-C_8)$-alkyl, COOH, $CO-O(C_1-C_8)$-alkyl, $CO-O-(C_3-C_8)$-cycloalkyl, $CO-NH_2$, $CO-NH(C_1-C_8)$-alkyl, $CO-N[(C_1-C_8)$-alkyl]$_2$, $(C_1-C_8)$-alkyl, $(C_3-C_8)$cycloalkyl, $(C_2-C_8)$-alkenyl, $(C_2-C_8)$-alkynyl, wherein on the alkyl, alkenyl and alkynyl groups, in each case, one to seven hydrogen atoms may be replaced by fluorine, or one hydrogen may be replaced by OH, $OC(O)CH_3$, $O-CH_2-Ph$, $NH_2$, $NH-CO-CH_3$, or $N(COOCH_2Ph)_2$;

an aryl radical wherein the aryl radical is phenyl, or 1- or 2-naphthyl; or a heterocycle wherein the heterocycle is 5-tetrazolyl, 1-[$(C_1-C_6)$-alkyl]-5-tetrazolyl, 2-[$(C_1-C_6)$-alkyl]-5-tetrazolyl, 1-imidazolyl, 1- or 4-[1,2,4]-triazolyl, 2- or 3-thienyl, 2- or 3-furyl, 2-, 3- or 4-pyridyl, 2-, 4- or 5-oxazolyl, 3-, 4- or 5-isoxazolyl, 2-, 4- or 5-thiazolyl, or 3-, 4- or 5-isothiazolyl, where the aryl radical or heterocycle may be substituted up to two times by F, Cl, Br, CN, OH, $(C_1-C_4)$-alkyl, $CF_3$, $O-(C_1-C_4)$-alkyl, $S(O)_{0-2}(C_1-C_6)$-alkyl, $NH_2$, $NH-SO_2-(C_1-C_4)$-alkyl, COOH, $CO-O-(C_1-C_4)$-alkyl, or $CO-NH_2$, and wherein on the alkyl groups, one to seven hydrogen atoms may be replaced by fluorine;

X is S, SO, or $SO_2$;

Y is $(CH_2)_p$, where p may be 0, 1, 2 or 3;

R5 is $CF_3$, $(C_1-C_{18})$-alkyl, $(C_3-C_4)$-cycloalkyl, or $(C_6-C_8)$-cycloalkyl, wherein, on the alkyl groups, one to seven hydrogen atoms may be replaced by fluorine; or R5 is $(CH_2)_r-COR6$, where r=1–6 and R6 may be OH, $O-(C_1-C_6)$-alkyl or $NH_2$; or R5 is $CH_2-CH(NHR7)-COR8$, where R7 may be H or $C(O)-(C_1-C_4)$-alkyl and R8 may be OH, $O-(C_1-C_6)$-alkyl or $NH_2$; or R5 is Phenyl, 1- or 2-naphthyl, biphenyl or a heterocyclic radical, where the rings or ring systems of the phenyl, 1- or 2-naphthyl or heterocyclic radical may be substituted up to two times by F, Cl, Br, I, CN, OH, $O(C_1-C_8)$-alkyl, $O(C_3-C_8)$-cycloalkyl, $O-CO-(C_1-C_8)$-alkyl, $O-CO-(C_3-C_8)$-cycloalkyl, $S(O)_{0-2}(C_1-C_8)$-alkyl, $S(O)_{0-2}(C_3-C_8)$-cycloalkyl, $NH_2$, $NH-(C_1-C_8)$-alkyl, $NH-(C_3-C_8)$-cycloalkyl, $N[(C_1-C_8)$-alkyl]$_2$, $N[(C_3-C_8)$-cycloalkyl]$_2$, $NH-CO-(C_2-C_8)$-alkyl, $NH-CO-(C_3-C_8)$-cycloalkyl; $SO_3H$, $SO_2-NH_2$, $SO_2-NH-(C_1-C_8)$-alkyl, $SO_2-NH-(C_3-C_8)$-cycloalkyl; $NH-SO_2-NH_2$, $NH-SO_2-(C_1-C_8)$-alkyl, $NH-SO_2-(C_3-C_8)$-cycloalkyl, $O-CH_2-COOH$, $O-CH_2-CO-O(C_1-C_8)$-alkyl, COOH, $CO-O(C_1-C_8)$-alkyl, $CO-O-(C_3-C_8)$-cycloalkyl, $CO-NH_2$, $CO-NH(C_1-C_8)$-alkyl, $CO-N[(C_1-C_8)$-alkyl]$_2$, $(C_1-C_8)$-alkyl, or $(C_3-C_8)$-cycloalkyl, wherein on the alkyl groups, in each case, one to seven hydrogen atoms may be replaced by fluorine;

R9 is F, Cl, Br, CN, $CF_3$, $(C_1-C_{18})$-alkyl, $(C_3-C_4)$-cycloalkyl, or $(C_6-C_8)$-cycloalkyl, wherein, on the alkyl groups, one to seven hydrogen atoms may be replaced by fluorine; or R9 is $(CH_2)_r-COR6$, where r=9–16 and R6 may be OH, $O-(C_1-C_6)$-alkyl or $NH_2$; or R9 is $CH_2-CH(NHR7)-COR8$ where R7 may be H or $C(O)-(C_1-C_4)$-alkyl and R8 may be OH, $O-(C_1-C_6)$-alkyl or $NH_2$; or R9 is $(CH_2)_u$-aryl or $(CH_2)_u$-heteroaryl, where u is 0 to 6 and aryl may be phenyl, 1- or 2-napthyl, biphenyl or a heterocyclic radical, where the rings or ring systems of aryl, heteroaryl or the heterocyclic radical may be substituted up to two times by F, Cl, Br, I, CN, OH, $O(C_1-C_8)$-alkyl, $O(C_3-C_8)$-cycloalkyl, $O-CO-(C_1-C_8)$-alkyl, $O-CO-(C_3-C_8)$-cycloalkyl, $S(O)_{0-2}(C_1-C_8)$-alkyl, $S(O)_{0-2}(C_3-C_8)$-cycloalkyl, $NH_2$, $NH-(C_1-C_8)$-alkyl, $NH-(C_3-C_8)$-cycloalkyl, $N[(C_1-C_8)$-alkyl]$_2$, $N[(C_3-C_8)$-cycloalkyl]$_2$, $NH-CO-(C_2-C_8)$- alkyl, NH—CO—($C_3$–$C_8$)-cycloalkyl; $SO_3H$, $SO_2$—$NH_2$, $SO_2$—NH—($C_1$–$C_8$)-alkyl, $SO_2$—NH—($C_3$–$C_8$)-cycloalkyl; NH—$SO_2$—$NH_2$, NH—$SO_2$—($C_1$–$C_8$)-alkyl, NH—$SO_2$—($C_3$–$C_8$)-cycloalkyl, O—$CH_2$—COOH, O—$CH_2$—CO—O($C_1$–$C_8$)-alkyl, COOH, CO—O($C_1$–$C_8$)-alkyl, CO—O—($C_3$–$C_8$)-cycloalkyl, CO—$NH_2$, CO—NH($C_1$–$C_8$)-alkyl, CO—N[($C_1$–$C_8$)-alkyl]$_2$, ($C_1$–$C_8$)-alkyl, ($C_3$–$C_8$)-cycloalkyl, wherein on the alkyl groups, in each case, one to seven hydrogen atoms may be replaced by fluorine;

and their physiologically acceptable salts;

provided that when R1, R2, R3 and R4 are all hydrogen, and X—Y—R5 is S-phenyl, then R9 is other than phenyl.

Preference is given to compounds of the formula I in which

R1, R2, R3, R4 independently of one another are H, F, Cl, Br, CN; $N_3$, $NO_2$, OH, O($C_1$–$C_8$)-alkyl, O($C_3$–$C_8$)-cycloalkyl, O—$CH_2$-phenyl, O-phenyl, O—CO—($C_1$–$C_8$)-alkyl, O—CO—($C_3$–$C_8$)-cycloalkyl, $NH_2$, NH—($C_1$–$C_8$)-alkyl, N[($C_1$–$C_8$)-alkyl]$_2$, COOH, CO—O($C_1$–$C_8$)-alkyl, ($C_1$–$C_8$)-alkyl, ($C_3$–$C_8$)cycloalkyl, ($C_2$–$C_8$)-alkenyl, ($C_2$–$C_8$)-alkynyl, wherein, on the alkyl, alkenyl and alkynyl groups, in each case, one to seven hydrogen atoms may be replaced by fluorine;

an aryl radical wherein the aryl radical is phenyl, or a heterocycle wherein the heterocycle is 1-imidazolyl, where the aryl radical or heterocycle may be substituted up to two times by F, Cl, Br, CN, OH, ($C_1$–$C_4$)-alkyl, $CF_3$, O—($C_1$–$C_4$)-alkyl, and wherein, on the alkyl groups, one to seven hydrogen atoms may be replaced by fluorine;

X is S, SO, $SO_2$;

Y is $(CH_2)_p$, where p may be 0, 1, 2 or 3;

R5 is $CF_3$, or ($C_1$–$C_{18}$)-alkyl, wherein, on the alkyl groups one to seven hydrogen atoms may be replaced by fluorine; or R5 is $(CH_2)_r$—COR6, where r is 1 to 6 and R6 may be OH, O—($C_1$–$C_6$)-alkyl or $NH_2$; or R5 is $CH_2$—CH(NHR7)-COR8, where R7 may be H or C(O)—($C_1$–$C_4$)-alkyl and R8 may be OH, O—($C_1$–$C_6$)-alkyl or $NH_2$; or R5 is Phenyl, 1- or 2-naphthyl, biphenyl or a heterocyclic radical, where the rings or ring systems may be substituted up to two times by F, Cl, Br, I, CN, OH, O($C_1$–$C_8$)-alkyl, O($C_3$–$C_8$)-cycloalkyl, O—CO—($C_1$–$C_8$)-alkyl, O—CO—($C_3$–$C_8$)-cycloalkyl, $S(O)_{0-2}$($C_1$–$C_8$)-alkyl, $S(O)_{0-2}$($C_3$–$C_8$)-cycloalkyl, $NH_2$, NH—($C_1$–$C_8$)-alkyl, NH—($C_3$–$C_8$)-cycloalkyl, N[($C_1$–$C_8$)-alkyl]$_2$, N[($C_3$–$C_8$)-cycloalkyl]$_2$, NH—CO—($C_2$–$C_8$)-alkyl, NH—CO—($C_3$–$C_8$)-cycloalkyl; $SO_3H$, $SO_2$—$NH_2$, $SO_2$—NH—($C_1$–$C_8$)-alkyl, $SO_2$—NH—($C_3$–$C_8$)-cycloalkyl; NH—$SO_2$—$NH_2$, NH—$SO_2$—($C_1$–$C_8$)-alkyl, NH—$SO_2$—($C_3$–$C_8$)-cycloalkyl, O—$CH_2$—COOH, O—$CH_2$—CO—O($C_1$–$C_8$)-alkyl, COOH, CO—O($C_1$–$C_8$)-alkyl, CO—O—($C_3$–$C_8$)-cycloalkyl, CO—$NH_2$, CO—NH($C_1$–$C_8$)-alkyl, CO—N[($C_1$–$C_8$)-alkyl]$_2$, ($C_1$–$C_8$)-alkyl, or ($C_3$–$C_8$)-cycloalkyl, wherein, on the alkyl groups, in each case, one to seven hydrogen atoms may be replaced by fluorine;

R9 is F, Cl, Br, CN, $CF_3$, ($C_1$–$C_{18}$)-alkyl, ($C_3$–$C_4$)-cycloalkyl, or ($C_6$–$C_8$)-cycloalkyl, wherein, on the alkyl groups, one to seven hydrogen atoms may be replaced by fluorine; or R9 is $(CH_2)_u$-aryl or $(CH_2)_u$-heteroaryl, where u is 0 to 6 and aryl may be phenyl, 1- or 2-napthyl, biphenyl or a heterocyclic radical, where the rings or ring systems of aryl, heteroaryl, or the heterocyclic radical may be substituted up to two times by F, Cl, Br, I, CN, OH, O($C_1$–$C_8$)-alkyl, O($C_3$–$C_8$)-cycloalkyl, O—CO—($C_1$–$C_8$)-alkyl, O—CO—($C_3$–$C_8$)-cycloalkyl, $S(O)_{0-2}$($C_1$–$C_8$)-alkyl, $S(O)_{0-2}$($C_3$–$C_8$)-cycloalkyl, $NH_2$, NH—($C_1$–$C_8$)-alkyl, NH—($C_3$–$C_8$)-cycloalkyl, N[($C_1$–$C_8$)-alkyl]$_2$, N[($C_3$–$C_8$)-cycloalkyl]$_2$, NH—CO—($C_2$–$C_8$)-alkyl, NH—CO—($C_3$–$C_8$)-cycloalkyl; $SO_3H$, $SO_2$—$NH_2$, $SO_2$—NH—($C_1$–$C_8$)-alkyl, $SO_2$—NH—($C_3$–$C_8$)-cycloalkyl; NH—$SO_2$—$NH_2$, NH—$SO_2$—($C_1$–$C_8$)-alkyl, NH—$SO_2$—($C_3$–$C_8$)-cycloalkyl, O—$CH_2$—COOH, O—$CH_2$—CO—O($C_1$–$C_8$)-alkyl, COOH, CO—O($C_1$–$C_8$)-alkyl, CO—O—($C_3$–$C_8$)-cycloalkyl, CO—$NH_2$, CO—NH($C_1$–$C_8$)-alkyl, CO—N[($C_1$–$C_8$)-alkyl]$_2$, ($C_1$–$C_8$)-alkyl, or ($C_3$–$C_8$)-cycloalkyl, wherein, on the alkyl groups, in each case, one to seven hydrogen atoms may be replaced by fluorine;

and their physiologically acceptable salts;

provided that when R1, R2, R3 and R4 are all hydrogen, and X—Y—R5 is S-phenyl, then R9 is other than phenyl.

Particular preference is given to compounds of the formula I in which

R1, R2, R3, R4 independently of one another are H, F, Cl, Br, CN; $N_3$, $NO_2$, OH, O($C_1$—$C_8$)-alkyl, O($C_3$–$C_8$)-cycloalkyl, O—$CH_2$-phenyl, O-phenyl, O—CO—($C_1$–$C_8$)-alkyl, O—CO—($C_3$–$C_8$)-cycloalkyl, $NH_2$, NH—($C_1$–$C_8$)-alkyl, N[($C_1$–$C_8$)-alkyl]$_2$, COOH, CO—O($C_1$–$C_8$)-alkyl, ($C_1$–$C_8$)-alkyl, ($C_3$–$C_8$)-cycloalkyl, ($C_2$–$C_8$)-alkenyl, ($C_2$–$C_8$)-alkynyl, wherein on the alkyl, alkenyl and alkynyl groups, in each case, one to seven hydrogen atoms may be replaced by fluorine, or an aryl radical wherein the aryl radical is phenyl, or heterocycle wherein heterocycle is 1-imidazolyl;

where the aryl radical or heterocycle may be substituted up to two times by F, Cl, Br, CN, OH, ($C_1$–$C_4$)-alkyl, $CF_3$, or O—($C_1$–$C_4$)-alkyl, and wherein, on the alkyl groups, one to seven hydrogen atoms may be replaced by fluorine;

X S, $SO_2$;

Y is $(CH_2)_p$, where p may be 0 or 1;

R5 is $CF_3$, or ($C_1$–$C_8$)-alkyl, wherein, on,the alkyl groups, one to seven hydrogen atoms may be replaced by fluorine; or R5 is phenyl, pyridinyl, where the rings of the phenyl and pyridinyl may be substituted up to two times by F, Cl, Br, or ($C_1$–$C_8$)-alkyl;

R9 is F, Cl, Br, ($C_1$–$C_8$)-alkyl, wherein, on, the alkyl groups, one to seven hydrogen atoms may be replaced by fluorine; or R9 is $(CH_2)_u$-phenyl, where phenyl may be substituted up to two times by F, Cl, Br, ($C_1$–$C_8$)-alkyl;

and their physiologically acceptable salts;

provided that when R1, R2, R3 and R4 are all hydrogen, and X—Y—R5 is S-phenyl, then R9 is other than phenyl.

The invention relates to compounds of the formula I in the form of their racemates, racemic mixtures and pure enantiomers, and also to their diastereomers and mixtures thereof.

The alkyl, alkenyl and alkynyl radicals in the substituents R1, R2, R3, R4, R5, R6, R7, R8 and R9 can be straight-chain or branched.

Heterocycle or heterocyclic radical is to be understood as meaning ring systems which, in addition to carbon, also contain heteroatoms, such as, for example, nitrogen, oxygen or sulfur. This definition furthermore includes ring systems in which the heterocycle or heterocyclic radical is fused with benzene rings. Preferred heterocycles or heterocyclic radicals are:
   heteroaryls, such as
   benzimidazolyl,
   1-[($C_1$–$C_6$)-alkyl]benzimidazolyl,
   imidazolyl,
   2- or 3-thienyl,
   2- or 3-furyl,
   benzoxazolyl,
   benzothiazolyl,
   2-, 3- or 4-pyridyl,
   pyrimidinyl,
   4-, 5- or 6-pyridazin-2H-yl-3-one,
   4-, 5- or 6-pyridazin-2-($C_1$–$C_8$)-alkyl-2H-yl-3-one,
   2-benzyl-4-, -5- or -6-pyridazin-2H-yl-3-one,
   3- or 4-pyridazinyl,
   2-, 3-, 4- or 8-quinolinyl,
   1-, 3- or 4-isoquinolinyl,
   1-phthalazinyl,
   3- or 4-cinnolinyl,
   2- or 4-quinazolinyl,
   2-pyrazinyl,
   2-quinoxalinyl,
   2-, 4- or 5-oxazolyl,
   3-, 4- or 5-isoxazolyl,
   2-, 4- or 5-thiazolyl,
   3-, 4- or 5-isothiazolyl,
   1-[($C_1$–$C_6$)-alkyl]-2-, -4- or -5-imidazolyl,
   3-, 4- or 5-pyrazolyl,
   1-[($C_1$–$C_6$)-alkyl]-3-, -4- or -5-pyrazolyl,
   1- or 4-[1,2,4]-triazolyl,
   4- or 5-[1,2,3]-triazolyl,
   1-[($C_1$–$C_6$)-alkyl]-4- or -5-[1,2,3]triazolyl,
   3-, 4- or 7-indolyl,
   N-[($C_1$–$C_6$)-alkyl]-3-, -4- or -7-indolyl
   2-[($C_1$–$C_6$)-alkyl]-3(2H)-indazolyl,
   1-[($C_1$–$C_6$)-alkyl]-3(1H)-indazolyl,
   5-tetrazolyl,
   1-[($C_1$–$C_6$)-alkyl]-1H-tetrazolyl,
   2-[($C_1$–$C_6$)-alkyl]-2H-tetrazolyl.

Physiologically acceptable salts, which may also be termed pharmaceutically acceptable salts, are particularly suitable for medical applications, due to their greater solubility in water compared with the starting or base compounds. Said salts must have a pharmaceutically acceptable anion or cation. Suitable pharmaceutically acceptable acid addition salts of the basic compounds of the invention are salts of inorganic acids such as hydrochloric acid, hydrobromic acid, phosphoric acid, metaphosphoric acid, nitric acid and sulfuric acid and also of organic acids such as, for example, acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid, tartaric acid and trifluoroacetic acid. For medicinal purposes, particular preference is given to using the chlorine salt. Suitable pharmaceutically acceptable basic salts of the acidic compounds of the invention are ammonium salts, alkali metal salts (such as sodium salts and potassium salts) and alkaline earth metal salts (such as magnesium salts and calcium salts).

Salts having a pharmaceutically unacceptable anion are likewise included within the scope of the present invention as useful intermediates for preparing or purifying compound of the invention and/or for use in nontherapeutic applications, for example in-vitro applications.

The term "physiologically functional derivative" used herein relates to any physiologically acceptable derivative of an inventive compound of the formula I, for example an ester which on administration to a mammal, for example humans, is capable of forming (directly or indirectly) a compound of the formula I or an active metabolite thereof.

The physiologically functional derivatives also include prodrugs of the compounds of the invention. Such prodrugs may be metabolized in vivo to a compound of the invention. These prodrugs may or may not be active themselves.

The physiologically functional derivatives furthermore include, for example, glucuronides, sulfuric acid esters, glycosides and ribosides.

The compounds of the invention may also be present in various polymorphous forms, for example as amorphous and crystalline polymorphous forms. All polymorphous forms of the compounds of the invention are included within the scope of the invention and are another aspect of the invention.

All references to "compound(s) according to formula (I)" refer hereinbelow to a compound/compounds of the formula (I) as described above and also to their salts, solvates and physiologically functional derivatives as described herein.

The amount of a compound according to formula (I) which is required in order to attain the desired biological effect, i.e., the pharmaceutically effective amount, depends on a number of factors, for example the specific compound selected, the intended use, the type of administration and the clinical state of the patient. In general, the daily dose is in the range from 0.3 mg to 100 mg (typically from 3 mg to 50 mg) per day per kilogram of body weight, for example 3–10 mg/kg/day. An intravenous dose can be, for example, in the range from 0.3 mg to 1.0 mg/kg and can be administered in a suitable manner as an infusion of 10 ng to 100 ng per kilogram per minute. Suitable infusion solutions for these purposes may contain, for example, from 0.1 ng to 10 mg, typically from 1 ng to 10 mg per milliliter. Individual doses may contain, for example, from 1 mg to 10 g of the active compound. Thus, ampules for injections can contain, for example, from 1 mg to 100 mg, and orally administerable individual dose formulations such as, for example, tablets or capsules can contain, for example, from 1.0 to 1000 mg, typically from 10 to 600 mg. In the case of pharmaceutically acceptable salts, the abovementioned masses relate to the mass of the compounds of the formula I on which the salt is based. The compound used for the prophylaxis or therapy of the abovementioned conditions may be the compounds according to formula (I) themselves, but they are preferably present in the form of a pharmaceutical composition together with an acceptable carrier. The carrier must be naturally acceptable, in the sense that it is compatible with the other ingredients of said composition and is not harmful to the patient's health. The carrier may be a solid or a liquid or both and is preferably formulated with the compound as an individual dose, for example as a tablet which may contain from 0.05% to 95% by weight of the active compound. Further pharmaceutically active substances may also be present, including further compounds according to formula (I). The pharmaceutical compositions of the invention may be prepared according to any of the known pharmaceutical methods which essentially comprise mixing the ingredients with pharmacologically acceptable carriers, which may also be termed pharmaceutically acceptable carriers and/or excipients.

Pharmaceutical compositions of the invention are those which are suitable for oral, rectal, topical, peroral (e.g. sublingual) and parenteral (e.g. subcutaneous, intramuscular, intradermal or intravenous) administration, although the most suitable manner of administration depends in each individual case on the nature and severity of the condition to be treated and on the nature of the compound according to formula (I) used in each case. Sugar-coated formulations and sugar-coated delayed-release formulations, too, are included within the scope of the invention. Preference is given to acid-resistant and enteric formulations. Suitable enteric coatings include cellulose acetate phthalate, polyvinyl acetate phthalate, hydroxypropylmethylcellulose phthalate and anionic polymers of methacrylic acid and methyl methacrylate.

Suitable pharmaceutical compositions for oral administration may be present in separate units as, for example, capsules, cachets, lozenges or tablets, which in each case contain a particular amount of the compound according to formula (I); as powders or granules; as solution or suspension in an aqueous or nonaqueous liquid; or as an oil-in-water or water-in-oil emulsion. As already mentioned, said compositions can be prepared according to any suitable pharmaceutical method which includes a step in which the active compound and the carrier (which may comprise one or more additional components) are contacted. In general, the compositions are prepared by uniform and homogeneous mixing of the active compound with a liquid and/or finely dispersed solid carrier, after which the product is shaped, if necessary. Thus a tablet, for example, may be prepared by pressing or shaping a powder or granules of the compound, where appropriate with one or more additional components. Pressed tablets can be prepared by tableting the compound in free-flowing form, for example a powder or granules, mixed, where appropriate, with a binder, lubricant, inert diluent and/or one or more surface active/dispersing agents in a suitable machine. Shaped tablets can be prepared by shaping the pulverulent compound, moistened with an inert liquid diluent, in a suitable machine.

Pharmaceutical compositions which are suitable for per-oral (sublingual) administration include lozenges which contain a compound according to formula (I) with a flavoring, usually sucrose and gum arabic or tragacanth, and pastilles which comprise the compound in an inert base such as gelatin and glycerol or sucrose and gum arabic.

Suitable pharmaceutical compositions for parenteral administration preferably comprise sterile aqueous preparations of a compound according to formula (I) which are preferably isotonic with the blood of the intended recipient. These preparations are preferably administered intravenously, although they may also be administered subcutaneously, intramuscularly or intradermally as an injection. Said preparations may preferably be prepared by mixing the compound with water and rendering the obtained solution sterile and isotonic with the blood. Injectable compositions of the invention generally contain from 0.1 to 5% by weight of the active compound.

Suitable pharmaceutical compositions for rectal administration are preferably present as individual dose suppositories. These may be prepared by mixing a compound according to formula (I) with one or more conventional solid carriers, for example cocoa butter, and shaping the resulting mixture.

Suitable pharmaceutical compositions for topical application to the skin are preferably present as ointment, cream, lotion, paste, spray, aerosol or oil. Carriers which may be used are petroleum jelly, lanolin, polyethylene glycols, alcohols and combinations of two or more of these substances. In general, the active compound is present at a concentration of from 0.1 to 15%, for example from 0.5 to 2%, by weight of the composition.

Transdermal administration is also possible. Suitable pharmaceutical compositions for transdermal administration may be present as individual patches which are suitable for long-term close contact with the epidermis of the patient. Such patches suitably contain the active compound in an optionally buffered aqueous solution, dissolved and/or dispersed in an adhesive or dispersed in a polymer. A suitable active compound concentration is from approx. 1% to 35%, preferably approx. 3% to 15%. A particular possibility is the release of the active compound by electro-transport or iontophoresis, as described, for example, in Pharmaceutical Research, 2(6): 318 (1986).

The invention furthermore provides a process for preparing the compounds of the formula I which comprises obtaining the compounds of the formula I by proceeding according to the reaction scheme below:

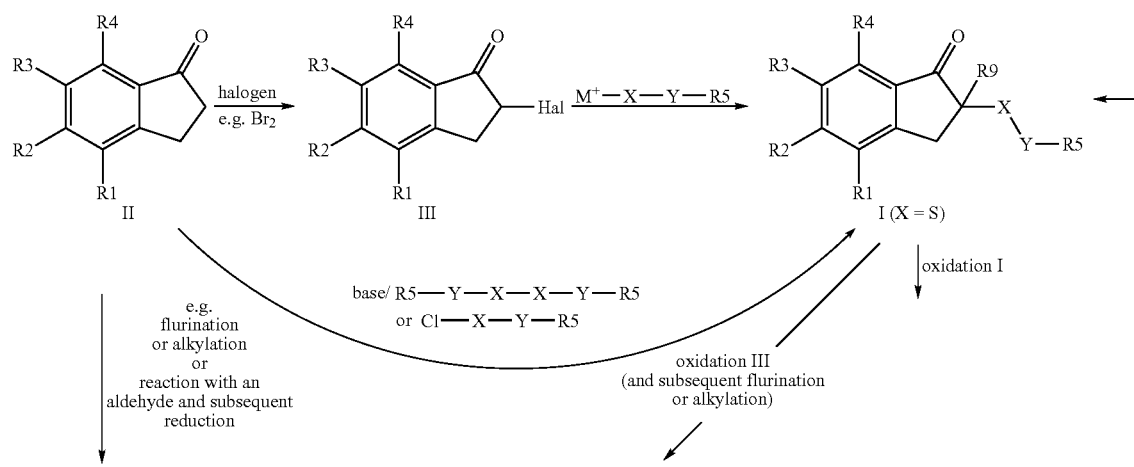

-continued

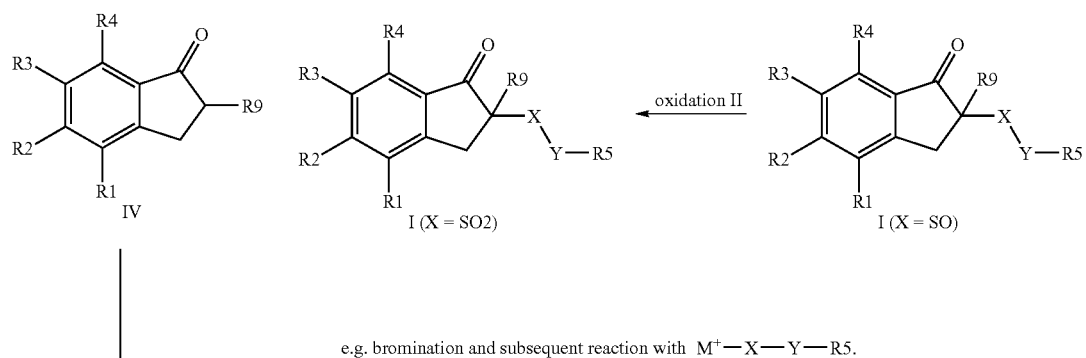

To this end, compounds of the formula II,

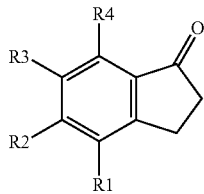

Formula II in which R1, R2, R3 and R4 are as defined above are converted with a halogen, such as, for example, bromine or chlorine, into a compound of the formula III. The compounds of the formula III are converted further with metal salts of thiols of the formula H—X—Y—R5, where X is sulfur and Y and R5 are as defined above into compounds of the formula I where X=S and R9=H. These metal salts can be employed as such or they can be generated in solution in situ from the thiol and a base, such as, for example, aqueous sodium hydroxide.

On the other hand, compounds of the formula I where X=S and R9=H can be obtained by reacting compounds of the formula II with a base, such as, for example, lithium diisopropylamide, for example in tetrahydrofuran, and with a disulfide of the formula R5-Y—X—X—Y—R5 in which R5 and Y are as defined above and X=S; alternatively, instead of the disulfide, it is also possible to use a sulfenyl chloride of the formula Cl—X—Y—R5 where X=S and Y and R5 are as defined above (see, for example, D. Seebach et al.; Chem. Ber. 109, 1601–1616 (1976)).

Compounds of the formula I in which X=S and R9 is not hydrogen can be obtained, for example, as follows: compounds of the formula II are subjected, for example, to a fluorination, alkylation or a condensation with an aldehyde and subsequent reduction, giving compounds of the formula IV which for their part can be converted, for example after bromination with the formula $M^+$—X—Y—R5, where X=S and Y and R5 are as defined above, to compounds of the formula I where X=S and R9 is not hydrogen.

Compounds of the formula I in which X=SO and R9 is not hydrogen can be prepared for example, by selective oxidation of the compound of the formula I in which X=S, using one equivalent of peroxytrifluoroacetic acid (C. G. Venier et al.; J. Org. Chem. 47, 3773 (1982)). The preparation of the sulfoxides from the sulfides can also be carried out using manganese dioxide or chromic acid (D. Edwards et al.; J. Chem. Soc. 1954, 3272). Furthermore suitable for this oxidation is hydrogen peroxide in acetic anhydride (A. V. Sviridova et al.; J. Org. Chem (Russ), English Transl.; 7, 2577 (1971)).

Compounds of the formula I in which X=SO$_2$ and R9 is not hydrogen can be obtained by oxidation using, for example, 2KHSO$_5$×KHSO$_4$×K$_2$SO$_4$ (Oxone), either from compounds of the formula I in which X=S and R9 is not hydrogen or from compounds of the formula I in which X=SO and R9 is not hydrogen (see, for example, M. Hudlický, Oxidations in Organic Chemistry, ACS Monograph 186, American Chemical Society, Washington, D.C., 1990).

Compounds of the formula I in which X=S, SO or SO$_2$ and R9 is not hydrogen, for example where R9 is phenyl, and Y is a bond and R5 is as described above can also be obtained by reacting compounds of the formula I in which X=S-phenyl and R9=H and Y is a bond and R5 is as described above with, for example, diphenyliodonium chloride. The resulting compounds can either be converted stepwise into the corresponding compounds in which X=SO or SO$_2$, or they are subsequently desulfurized with zinc/acetic acid and are then available for further reactions according to the scheme above.

Compounds of the formula I in which X=SO or SO$_2$, R9=H and Y=a bond (=(CH$_2$)m where m=0) can also, alternatively, be prepared according to the scheme below (shown for the preparation of the aryl sulfoxides (H. J. Monteiro et al.; Tetrahedron Letters 11, 921–924 (1975) and aryl sulfones (A. K. Maiti et al.; Tetrahedron 50, 10483–10490 (1994)):

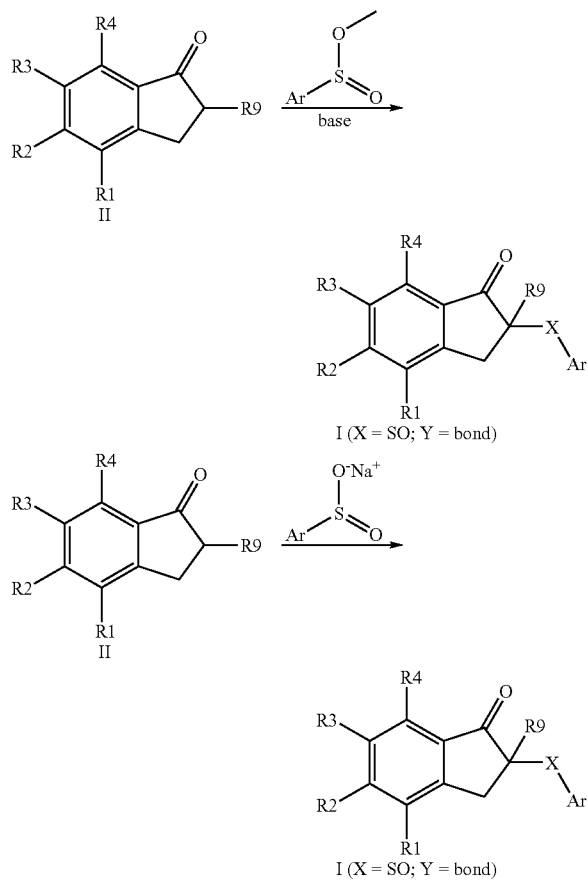

Compounds of the formula I in which X=SO₂ and R9 is not hydrogen and Y and R5 are as defined above can also be obtained by subjecting compounds of the formula I in which X=SO₂ and R9=H and Y and R5 are as defined above to a fluorination or alkylation, for example.

Inorganic acids suitable for forming salts are, for example: hydrohalic acids, such as hydrochloric acid and hydrobromic acid, and also sulfuric acid, phosphoric acid and amidosulfonic acid.

Organic acids suitable for salt formation which may be mentioned are, for example: formic acid, acetic acid, benzoic acid, p-toluenesulfonic acid, benzenesulfonic acid, succinic acid, fumaric acid, maleic acid, lactic acid, tartaric acid, citric acid, L-ascorbic acid, salicylic acid, isethionic acid, methanesulfonic acid, trifluoromethanesulfonic acid, 1,2-benzisothiazol-3(2H)-one, 6-methyl-1,2,3-oxathiazin-4(3H)-one 2,2-dioxide.

The examples shown below serve to illustrate the invention without limiting it. The melting points or decomposition points (m.p.) measured are uncorrected and generally depend on the heating rate.

The retention times given in the table below refer to the following methods for determination:

Method A: Column: Merck, LiChroCart 55-2, PuroSpher STAR, RP 18 e; measured at 254 nm; gradient: solvent A acetonitrile/water 90:10+0.5% formic acid; solvent B acetonitrile/water 10:90+0.5% formic acid; flow rate: 0.750 ml/min; time (min)/solvent B (%): 0.00/95.0, 0.50/95.0, 1.75/5.0, 4.25/5.0, 4.50/95.0, 5.00/95.0; temperature: 40° C.:

Method B: column: YMC J'sphere, 33×2, ODS H 80 4µ; measured at 254 nm; gradient: solvent A acetonitrile+ 0.5% formic acid; solvent B water+0.5% formic acid; flow rate: 1.00 ml/min; time (min)/solvent B (%): 0.00/90.0, 2.50/5.0, 3.30/5.0, 3.35/90.0; temperature: 30° C.:

TABLE 1

Examples

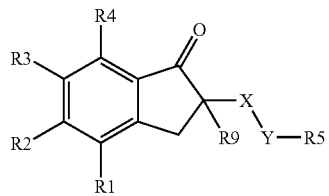

Formula I

| Example | R1 | R2 | R3 | R4 | X | Y | R5 | R9 | m.p.[° C.] |
|---|---|---|---|---|---|---|---|---|---|
| 1 | H | Cl | H | H | SO₂ | — | CH₃ | F | 150 [MH⁺] |
| 2 | H | Cl | H | H | SO₂ | — | CH₃ | CH₂Ph | 335.2 |
| 3 | H | OCH₃ | OCH₃ | H | SO₂ | — | CH₃ | F | 289.2 |

Retention time in min (method A or B

| 4 | H | Cl | H | H | S | — | Pyridin-2-yl | F | 2.789 (A) |
| 5 | H | Cl | H | H | S | CH₂ | CF₃ | F | 2.699 (B) |
| 6 | H | H | H | H | S | — | C₆H₄-4-Cl | F | 3.096 (A) |
| 7 | H | Cl | H | H | SO₂ | — | Pyridin-2-yl | F | 1.460 (B) |

TABLE 1-continued

Examples

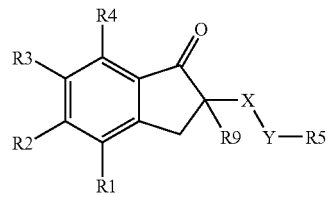

Formula I

| Example | R1 | R2 | R3 | R4 | X | Y | R5 | R9 | m.p.[° C.] |
|---|---|---|---|---|---|---|---|---|---|
| 8 | H | Cl | H | H | $SO_2$ | $CH_2$ | $CF_3$ | F | 1.514 (B) |
| 9 | H | $C_6H_4$-4-Cl | H | H | $SO_2$ | — | $CH_3$ | F | 2.628 (B) |
| 10 | H | $CF_3$ | H | H | $SO_2$ | — | $CH_3$ | F | 2.261 (B) |
| 11 | H | H | $C_6H_4$-4-$CF_3$ | H | $SO_2$ | — | $CH_3$ | F | 2.656 (B) |
| 12 | Br | H | H | H | $SO_2$ | — | $CH_3$ | F | 2.182 (B) |
| 13 | H | N-phthalimidoyl | H | H | $SO_2$ | — | $CH_3$ | F | 2.221 (B) |

The compounds of the formula I are distinguished by beneficial actions on the metabolism of lipids, and they are particularly suitable for weight reduction and, after weight reduction, for maintaining a reduced weight in mammals and as anorectic agents. The compounds are distinguished by their low toxicity and their few side effects. The compounds may be employed alone or in combination with other weight-reducing or anorectic active compounds. Further anorectic active compounds of this kind are mentioned, for example, in the Rote Liste, Chapter 01 under weight-reducing agents/appetite suppressants, and may also include those active compounds which increase the energy turnover of the organism and thus lead to weight reduction or else those which influence the general metabolism of said organism such that increased calorie intake does not cause an enlargement of the fat depots and a normal calorie intake causes a reduction in the fat depots of said organism. The compounds are suitable for the prophylaxis and, in particular, for the treatment of problems of excess weight or obesity. The compounds are furthermore suitable for the prophylaxis and, in particular, for the treatment of type II diabetes, of arteriosclerosis and for the normalization of lipid metabolism and for the treatment of high blood pressure.

In a further aspect of the invention, the compounds of the formula I may be administered in combination with one or more further pharmacologically active substances which may be selected, for example, from the group consisting of antidiabetics, antiadipose agents, blood-pressure-lowering active compounds, lipid reducers and active compounds for the treatment and/or prevention of complications caused by diabetes or associated with diabetes.

Suitable antidiabetics include insulins, amylin, GLP-1 and GLP-2 derivatives such as, for example, those disclosed by Novo Nordisk A/S in WO 98/08871 and also oral hypoglycemic active compounds.

Said oral hypoglycemic active compounds preferably include sulfonyl ureas, biguanides, meglitinides, oxadiazolidinediones, thiazolidinediones, glucosidase inhibitors, glucagon receptor antagonists, GLP-1 agonists, potassium channel openers such as, for example, those disclosed by Novo Nordisk A/S in WO 97/26265 and WO 99/03861, insulin sensitizers, activators of insulin receptor kinase, inhibitors of liver enzymes involved in the stimulation of gluconeogenesis and/or glycogenolysis, for example glycogen phosphorylase inhibitors, modulators of glucose uptake and glucose elimination, lipid metabolism-modifying compounds such as antihyperlipidemic active compounds and antilipidemic active compounds, for example HMGCoA-reductase inhibitors, inhibitors of cholesterol transport/cholesterol uptake, inhibitors of the reabsorption of bile acid or inhibitors of microsomal triglyceride transfer protein (MTP), compounds which reduce food intake, PPAR and RXR agonists and active compounds which act on the ATP-dependent potassium channel of beta cells.

In one embodiment of the present invention, the present compounds are administered in combination with insulin.

In another embodiment, the compounds of the invention are administered in combination with a sulfonylurea such as, for example, tolbutamide, glibenclamide, glimepiride, glipizide, gliquidone, glisoxepide, glibornuride or gliclazide.

In another embodiment, the compounds of the present invention are administered in combination with a biguanide such as, for example, metformin.

In another embodiment, the compounds of the present invention are administered in combination with a meglitinide such as, for example, repaglinide.

In yet another embodiment, the compounds of the present invention are administered in combination with a thiazolidinedione such as, for example, troglitazone, ciglitazone, pioglitazone, rosiglitazone or the compounds disclosed by Dr. Reddy's Research Foundation in WO 97/41097, in particular 5-[[4-[(3,4-dihydro-3-methyl-4-oxo-2-quinazolinylmethoxy]phenyl]methyl]-2,4-thiazolidinedione.

In yet another embodiment, the compounds of the present invention are administered in combination with a monoamine oxidase inhibitor such as disclosed, for example, in WO 01/12176. Particularly suitable for this purpose are [3(S),3a(S)]-3-methoxymethyl-7-[4,4,4-trifluorobutoxy]-3,3a,4,5-tetrahydro-1H-oxazolo[3,4-a]quinolin-1-one, (R)-5-(methoxymethyl)-3-[6-(4,4,4-trifluorobutoxy)benzofuran-3-yl]oxazolidin-2-one or (R)-5-(methoxymethyl)-3-[6-cyclopropylmethoxybenzofuran-3-yl]oxazolidin-2-one.

In another embodiment, the compounds of the present invention are administered in combination with an α-glucosidase inhibitor such as, for example, miglitol or acarbose.

In yet another embodiment, the present compounds are administered in combination with an hCNTF (human ciliary neurotrophic factor) or derivatives thereof, such as, for example, $CNTF_{AX15}$ or modified $CNTF_{AX15}$, such as disclosed, for example, in Lambert et al., PNAS 98, 4652–4657.

In another embodiment, the compounds of the present invention are administered in combination with an active compound which acts on the ATP-dependent potassium channel of the beta cells, such as, for example, tolbutamide, glibenciamide, glimepiride, glipizide, gliclazide or repaglinide.

In yet another embodiment, the compounds of the present invention are administered in combination with an antihyperlipidemic active compound or an antilipidemic active compound such as, for example, cholestyramine, colestipol, clofibrate, gemfibrozil, lovastatin, pravastatin, simvastatin, atorvastatin, cerivastatin, fluvastatin, probucol, ezetimibe or dextrothyroxine.

In another embodiment, the compounds of the present invention are administered in combination with more than one of the aforementioned compounds, for example in combination with a sulfonylurea and metformin, a sulfonylurea and acarbose, repaglinide and mefformin, insulin and a sulfonylurea, insulin and metformin, insulin and troglitazone, insulin and lovastatin, etc.

Furthermore, the compounds of the invention may be administered in combination with one or more antiadipose agents or appetite-controlling active compounds.

Such active compounds may be selected from the group consisting of CART agonists, NPY antagonists, melanocortin 3 or 4 (MC3 or MC4) agonists, melanin-concentrating hormone (MCH) antagonists, orexin antagonists, H3 agonists, TNF agonists, CRF agonists, CRF BP antagonists, urocortin agonists, β3 adrenoceptor agonists, CCK agonists, serotonin re-uptake inhibitors, mixed serotonin and noradrenalin reuptake inhibitors, 5HT modulators, bombesin agonists, galanin antagonists, glucocorticoid receptor modulators, growth hormone, growth-hormone-releasing compounds, TRH agonists, uncoupling protein 2 or 3 modulators, leptin receptor agonists, leptin mimetics, dopamine agonists (bromocriptine, doprexin), lipase/amylase inhibitors, cannabinoid receptor 1 antagonists, modulators of acylation-stimulating protein (ASP), PPAR modulators, RXR modulators or TR-β agonists.

In one embodiment of the invention, the antiadipose agent is leptin or modified leptin.

In another embodiment, the antiadipose agent is dexamphetamine or amphetamine.

In another embodiment, the antiadipose agent is fenfluramine or dexfenfluramine.

In yet another embodiment, the antiadipose agent is sibutramine or the mono- and bis-demethylated active metabolite of sibutramine.

In another embodiment, the antiadipose agent is orlistate.

In another embodiment, the antiadipose agent is mazindol, diethylpropione or phentermine.

Furthermore, the compounds of the present invention may be administered in combination with one or more antihypertensive active compounds. Examples of antihypertensive active compounds are betablockers such as alprenolol, atenol, timolol, pindolol, propanolol and metoprolol, ACE (angiotensin-converting enzyme) inhibitors such as, for example, benazepril, captopril, enalapril, fosinopril, lisinopril, quinapril and rampril, calcium channel blockers such as nifedipine, felodipine, nicardipine, isradipine, nimodipine, diltiazem and verapamil, and also alphablockers such as doxazosin, urapidil, prazosin and terazosin. Furthermore, reference may be made to Remington: The Science and Practice of Pharmacy, 19th edition, Gennaro, editor, Mack Publishing Co., Easton, Pa., 1995.

The present invention provides for methods for reducing weight in mammals in need thereof, methods for the prophylaxis or treatment of obesity in mammals in need thereof, and methods for the prophylaxis or treatment of type II diabetes in mammals in need thereof, comprising administering to such mammals pharmaceutically effective amounts of compounds of the present invention.

The present invention provides also for methods for reducing weight in mammals in need thereof, methods for the prophylaxis or treatment of obesity in mammals in need thereof, and methods for the prophylaxis or treatment of type II diabetes in mammals in need thereof, comprising administering to such mammals pharmaceutically effective amounts of compounds of the present invention, in combination with pharmaceutically effective amounts of further pharmacologically active compounds suitable for reducing weight in mammals.

It is self-evident that every suitable combination of the compounds of the invention with one or more of the aforementioned compounds and optionally one or more other pharmacologically active substances is to be regarded as covered by the scope of protection of the present invention.

The activity of the compounds was assayed as follows:

Biological Test Model:

The anorectic action was tested on female NMRI mice. After removal of feed for 24 hours, the preparation to be tested was administered intraperitoneally (ip) or by gavage (po). The animals were housed singly and, with free access to drinking water, they were offered evaporated milk 30 minutes after administration of the preparation. The consumption of evaporated milk was determined and the general behavior of the animals was monitored every half an hour for 7 hours. The measured milk consumption was compared to that of vehicle-treated control animals.

TABLE 2

Anorectic action, measured as a reduction in the cumulative milk consumption by treated animals compared with control animals Compound/Example Formula I (structure with R1, R2, R3, R4, R9, X, Y—R5, and ketone)

| Formula I | Dose [mg/kg] | Number of animals/ cumulative milk consumption by treated animals N/[ml] | Number of animals/ cumulative milk consumption by untreated control animals N/[ml] | Reduction in cumulative milk consumption as % of the control |
| --- | --- | --- | --- | --- |
| Example 1 | 20 | 5/2.00 | 5/3.86 | 48 |

The table indicates that the compounds of the formula I exhibit very good anorectic action.

The preparation of some-examples is described in detail below; the other compounds of the formula I were obtained analogously:

EXAMPLE 1

5-Chloro-2-fluoro-2-methanesulfonylindan-1-one 1. 5-Chloro-2-methylsulfanylindan-1-one:

0.98 g (4 mmol) of 2-bromo-5-chloroindan-1-one and 0.42 g (6 mmol) of sodium thiomethoxide are suspended in 5 ml of ethanol, treated in an ultrasonic bath for 30 minutes and then stirred at room temperature for 90 minutes. The reaction mixture is concentrated under reduced pressure and chromatographed on silica gel using toluene/ethyl acetate 10/1. The eluates are concentrated under reduced pressure, giving 5-chloro-2-methylsulfanylindan-1-one of melting point 90° C.

2. 5-Chloro-2-methanesulfonylindan-1-one:

0.5 g (2.35 mmol) of 5-chloro-2-methylsulfanylindan-1-one is dissolved in 10 ml of methanol; at 0° C., a solution of 4.33 g (7.05 mmol) of $2KHSO_5 \times KHSO_4 \times K_2SO_4$ in 10 ml of water is added dropwise. The mixture is stirred at room temperature for 5 h; the methanol is distilled off and the aqueous residue is extracted with dichloromethane. The organic phase is separated off, dried over $MgSO_4$, filtered and concentrated under reduced pressure. This gives 0.5 g of 5-chloro-2-methanesulfonylindan-1-one of melting point 197° C.

3. 5-Chloro-2-fluoro-2-methanesulfonylindan-1-one:

0.734 g (3 mmol) of 5-chloro-2-methanesulfonylindan-1-one and 1.77 g (5 mmol) of N-fluoro-N'-(chloromethyl)triethylenediamine bis(tetrafluoroborate) are suspended in a mixture of 2.5 ml of water and 7.5 ml of acetonitrile and stirred under reflux for 4 h. The reaction mixture is cooled, concentrated under reduced pressure and purified chromatographically on silica gel using the mobile phase dichloromethane. This gives 5-chloro-2-fluoro-2-methanesulfonylindan-1-one of melting point 150° C.

EXAMPLE 2

2-Benzyl-5-chloro-2-methanesulfonylindan-1-one

1. Methyl 2-benzyl-5-chloro-1-oxoindane-2-carboxylate:

1.11 ml of diisopropylamine are dissolved in 25 ml of dry tetrahydrofuran, 6.9 ml of N-butyllithium in n-hexane (15%) are added at −50° C., and the mixture is stirred at −10° C. for 20 minutes. At −50° C., 2.25 g of methyl 5-chloro-1-oxoindane-2-carboxylate, dissolved in 25 ml of tetrahydrofuran, are then added dropwise. The mixture is stirred at −50° C. for 30 min, and a solution of 1.31 ml of benzyl bromide in 5 ml of tetrahydrofuran is then added dropwise. The reaction mixture is stirred at room temperature for 20 h. To bring the reaction to completion, another 1.31 ml of benzyl bromide are added and the mixture is heated under reflux for 72 h. 20 ml of saturated sodium bicarbonate solution are added to the reaction mixture, which is then diluted with ethyl acetate. The organic phase is separated off, washed with saturated sodium chloride solution, dried over magnesium sulfate, filtered and concentrated under reduced pressure. This gives methyl 2-benzyl-5-chloro-1-oxoindane-2-carboxylate having a molecular weight of 314 ($C_{18}H_{15}ClO_3$); MS (ESI): 315.1 (MH$^+$).

2. 2-Benzyl-5-chloroindan-1-one:

The compound of example 2.1 is suspended in a mixture of 10 ml of ethanol and 10 ml of 5% strength aqueous sodium hydroxide solution and stirred at 40° C. for one hour. The alcohol is then removed under reduced pressure and the residue is extracted with ethyl acetate. The organic phase is washed with water until neutral, dried over magnesium sulfate, filtered and concentrated under reduced pressure. The residue is purified chromatographically on silica gel using n-heptane/ethyl acetate 2/1. This gives 2-benzyl-5-chloroindan-1-one having a molecular weight of 256 ($C_{16}H_{13}ClO$); MS (ESI): 256.8 (MH$^+$).

3. 2-Benzyl-2-bromo-5-chloroindan-1-one:

0.86 g of the compound of example 2.2 is dissolved in 4 ml of acetic acid, 50 µl of 48% strength HBr solution and 0.207 ml of bromine are added and the mixture is stirred at room temperature for one hour. The crude product is purified chromatographically on silica gel using toluene. This gives 2-benzyl-2- bromo-5-chloroindan-1-one having a molecular weight of 334 ($C_{16}H_{12}BrClO$); MS (ESI): 334.8 (MH$^+$).

4. 2-Benzyl-5-chloro-2-methanesulfonylindan-1-one:

1 mmol of the compound of example 2.3 and 1.2 mmol of methanesulfinic acid sodium salt in 3 ml of dimethylformamide are stirred at 70° C. for 4 hours. The crude product is purified chromatographically on silica gel using n-heptane/ethyl acetate 1/1. This gives 2-benzyl-5-chloro-2-methanesulfonylindan-1-one of molecular weight 334 ($C_{17}H_{15}ClO_3S$); MS (ESI): 335.2 (MH$^+$).

The compounds of examples 4–6 are obtained by reacting the corresponding 2-fluroindan-1-one with the sodium salt of the corresponding mercaptan.

The compounds of examples 7–13 are obtained as described in example 1.3 by fluorination of the corresponding sulfonyl derivatives.

What is claimed is:

1. A compound of the formula I

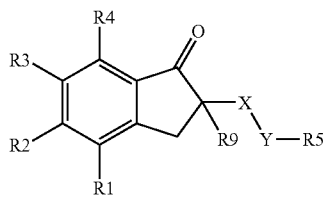

I wherein:

R1, R2, R3, R4 independently of one another are H, F, Cl, Br, I, CN; $N_3$, $NO_2$, OH, O($C_1$–$C_8$)-alkyl, O($C_3$–$C_8$)-cycloalkyl, O—$CH_2$-phenyl, O-phenyl, O—CO—($C_1$–$C_8$)-alkyl, O—CO—($C_3$–$C_8$)-cycloalkyl, S(O)$_{0-2}$($C_1$–$C_8$)-alkyl, S(O)$_{0-2}$($C_3$–$C_8$)-cycloalkyl, $NH_2$, NH—($C_1$–$C_8$)-alkyl, NH—($C_3$–$C_8$)-cycloalkyl, N[($C_1$–$C_8$)-alkyl]$_2$, N[($C_3$–$C_8$)-cycloalkyl]$_2$, NH—CO—($C_1$–$C_8$)-alkyl, NH—CO—($C_3$–$C_8$)-cycloalkyl; $SO_3H$, $SO_2$—$NH_2$, SO2-NH—($C_1$–$C_8$)-alkyl, $SO_2$—NH—($C_3$–$C_8$)-cycloalkyl, NH—$SO_2$—$NH_2$, NH—$SO_2$—($C_1$–$C_8$)-alkyl, NH—$SO_2$—($C_3$–$C_8$)-cycloalkyl, O—$CH_2$—COOH, O—$CH_2$—CO—O($C_1$–$C_8$)-alkyl, COOH, CO—O($C_1$–$C_8$)-alkyl, CO—O—($C_3$–$C_8$)-cycloalkyl, CO—$NH_2$, CO—NH($C_1$–$C_8$)-alkyl, CO—N[($C_1$–$C_8$)-alkyl]$_2$, ($C_1$–$C_8$)-alkyl, ($C_3$–$C_8$)cycloalkyl, ($C_2$–$C_8$)-alkenyl, ($C_2$–$C_8$)-alkynyl, wherein on the alkyl, alkenyl and alkynyl groups, in each case, one to seven hydrogen atoms may be replaced by fluorine, or one hydrogen may be replaced by OH, OC(O)$CH_3$, O—$CH_2$—Ph, $NH_2$, NH—CO—$CH_3$ or N(COOCH$_2$Ph)$_2$;

an aryl radical wherein the aryl radical is phenyl, or 1- or 2-naphthyl; or a heterocycle wherein the heterocycle is 5-tetrazolyl, 1-[($C_1$–$C_6$)-alkyl]-5-tetrazolyl, 2-[($C_1$–$C_6$)-alkyl]-5-tetrazolyl,
1-imidazolyl,
1- or 4-[1,2,4]-triazolyl,
2- or 3-thienyl,
2- or 3-furyl,
2-, 3- or 4-pyridyl,
2-, 4- or 5-oxazolyl,
3-, 4- or 5-isoxazolyl,
2-, 4- or 5-thiazolyl, or
3-, 4- or 5-isothiazolyl, where the aryl radical or heterocycle may be substituted up to two times by F, Cl, Br, CN, OH, ($C_1$–$C_4$)-alkyl, $CF_3$, O—($C_1$–$C_4$)-alkyl, S(O)$_{0-2}$($C_1$–$C_6$)-alkyl, $NH_2$, NH—$SO_2$—($C_1$–$C_4$)-alkyl, COOH, CO—O—($C_1$–$C_4$)-alkyl, or CO—$NH_2$, and wherein on the alkyl groups, one to seven hydrogen atoms may be replaced by fluorine;

X is S, SO, or $SO_2$;

Y is $(CH_2)_p$, where p may be 0, 1, 2 or 3;

R5 is $CF_3$, ($C_1$–$C_{18}$)-alkyl, ($C_3$–$C_4$)-cycloalkyl, or ($C_6$–$C_8$)-cycloalkyl, wherein, on the alkyl groups, one to seven hydrogen atoms may be replaced by fluorine;

or R5 is $(CH_2)_r$—COR6, where r=1–6 and R6 may be OH, O—($C_1$–$C_6$)-alkyl or $NH_2$;

or R5 is $CH_2$—CH(NHR7)-COR8, where R7 may be H or C(O)—($C_1$–$C_4$)-alkyl and R8 may be OH, O—($C_1$–$C_6$)-alkyl or $NH_2$;

or R5 is phenyl, 1- or 2-naphthyl, biphenyl or a heterocyclic radical, where the rings or ring systems of the phenyl, 1- or 2-naphthyl or heterocyclic radical may be substituted up to two times by F, Cl, Br, I, CN, OH, O($C_1$–$C_8$)-alkyl, O($C_3$–$C_8$)-cycloalkyl, O—CO—($C_1$–$C_8$)-alkyl, O—CO—($C_3$–$C_8$)-cycloalkyl, S(O)$_{0-2}$($C_1$–$C_8$)-alkyl, S(O)$_{0-2}$($C_3$–$C_8$)-cycloalkyl, $NH_2$, NH—($C_1$–$C_8$)-alkyl, NH—($C_3$–$C_8$)-cycloalkyl, N[($C_1$–$C_8$)-alkyl]$_2$, N[($C_3$–$C_8$)-cycloalkyl]$_2$, NH—CO—($C_2$–$C_8$)-alkyl, NH—CO—($C_3$–$C_8$)-cycloalkyl; $SO_3H$, $SO_2$—$NH_2$, $SO_2$—NH—($C_1$–$C_8$)-alkyl, $SO_2$—NH—($C_3$–$C_8$)-cycloalkyl; NH—$SO_2$—$NH_2$, NH—$SO_2$—($C_1$–$C_8$)-alkyl, NH—$SO_2$—($C_3$–$C_8$)-cycloalkyl, O—$CH_2$—COOH, O—$CH_2$—CO—O($C_1$–$C_8$)-alkyl, COOH, CO—O($C_1$–$C_8$)-alkyl, CO—O—($C_3$–$C_8$)-cycloalkyl, CO—$NH_2$, CO—NH($C_1$–$C_8$)-alkyl, CO—N[($C_1$–$C_8$)-alkyl]$_2$, ($C_1$–$C_8$)-alkyl, or ($C_3$–$C_8$)-cycloalkyl, wherein on the alkyl groups, in each case, one to seven hydrogen atoms may be replaced by fluorine;

R9 is F, Cl, Br, CN, $CF_3$, ($C_1$–$C_{18}$)-alkyl, ($C_3$–$C_4$)-cycloalkyl, or ($C_6$–$C_8$)-cycloalkyl, wherein, on the alkyl groups, one to seven hydrogen atoms may be replaced by fluorine;

or R9 is $(CH_2)_r$—COR6, where r=9–16 and R6 may be OH, O—($C_1$–$C_6$)-alkyl or $NH_2$;

or R9 is $CH_2$—CH(NHR7)-COR8 where R7 may be H or C(O)—($C_1$–$C_4$)-alkyl and R8 may be OH, O—($C_1$–$C_6$)-alkyl or $NH_2$;

or R9 is $(CH_2)_u$-aryl or $(CH_2)_u$-heteroaryl, where u is 0 to 6 and aryl may be phenyl, 1- or 2-napthyl, biphenyl or a heterocyclic radical, where the rings or ring systems of aryl, heteroaryl or the heterocyclic radical may be substituted up to two times by F, Cl, Br, I, CN, OH, O($C_1$–$C_8$)-alkyl, O($C_3$–$C_8$)-cycloalkyl, O—CO—($C_1$–$C_8$)-alkyl, O—CO—($C_3$–$C_8$)-cycloalkyl, S(O)$_{0-2}$($C_1$–$C_8$)-alkyl, S(O)$_{0-2}$($C_3$–$C_8$)-cycloalkyl, $NH_2$, NH—($C_1$–$C_8$)-alkyl, NH—($C_3$–$C_8$)-cycloalkyl, N[($C_1$–$C_8$)-alkyl]$_2$, N[($C_3$–$C_8$)-cycloalkyl]$_2$, NH—CO—($C_2$–$C_8$)-alkyl, NH—CO—($C_3$–$C_8$)-cycloalkyl; $SO_3H$, $SO_2$—$NH_2$, $SO_2$—NH—($C_1$–$C_8$)-alkyl, $SO_2$—NH—($C_3$–$C_8$)-cycloalkyl; NH—$SO_2$—$NH_2$, NH—$SO_2$—($C_1$–$C_8$)-alkyl, NH—$SO_2$—($C_3$–$C_8$)-cycloalkyl, O—$CH_2$—COOH, O—$CH_2$—CO—O($C_1$–$C_8$)-alkyl, COOH, CO—O($C_1$–$C_8$)-alkyl, CO—O—($C_3$–$C_8$)-cycloalkyl, CO—$NH_2$, CO—NH($C_1$–$C_8$)-alkyl, CO—N[($C_1$–$C_8$)-alkyl]$_2$, ($C_1$–$C_8$)-alkyl, ($C_3$–$C_8$)- cycloalkyl, wherein on the alkyl groups, in each case, one to seven hydrogen atoms may be replaced by fluorine;
or a physiologically acceptable salt thereof;
provided that when R1, R2, R3 and R4 are all hydrogen, and X—Y—R5 is —S-phenyl, then R9 is other than phenyl; and that when R1, R2, R3 and R4 are all hydrogen, and X—Y—R5 is —S-benzyl-4-carboxy, then R9 is other than methyl.

2. A compound according to claim 1 of the formula I, wherein
R1, R2, R3, R4 independently of one another are H, F, Cl, Br, CN; $N_3$, $NO_2$, OH, $O(C_1-C_8)$-alkyl, $O(C_3-C_8)$-cycloalkyl, O—$CH_2$-phenyl, O-phenyl, O—CO—$(C_1-C_8)$-alkyl, O—CO—$(C_3-C_8)$-cycloalkyl, $NH_2$, NH—$(C_1-C_8)$-alkyl, $N[(C_1-C_8)$-alkyl$]_2$, COOH, CO—$O(C_1-C_8)$-alkyl, $(C_1-C_8)$-alkyl, $(C_3-C_8)$cycloalkyl, $(C_2-C_8)$-alkenyl, $(C_2-C_8)$-alkynyl, wherein, on the alkyl, alkenyl and alkynyl groups, in each case, one to seven hydrogen atoms may be replaced by fluorine;
an aryl radical wherein the aryl radical is phenyl,
or a heterocycle wherein the heterocycle is 1-imidazolyl,
where the aryl radical or heterocycle may be substituted up to two times by F, Cl, Br, CN, OH, $(C_1-C_4)$-alkyl, $CF_3$, O—$(C_1-C_4)$-alkyl, and wherein, on the alkyl groups, one to seven hydrogen atoms may be replaced by fluorine;
X is S, SO, $SO_2$;
Y is $(CH_2)_p$, where p may be 0, 1, 2 or 3;
R5 is $CF_3$, or $(C_1-C_{18})$-alkyl, wherein, on the alkyl groups one to seven hydrogen atoms may be replaced by fluorine;
or R5 is $(CH_2)_r$—COR6, where r is 1 to 6 and R6 may be OH, O—$(C_1-C_6)$-alkyl or $NH_2$;
or R5 is $CH_2$—CH(NHR7)-COR8, where R7 may be H or C(O)—$(C_1-C_4)$-alkyl and R8 may be OH, O—$(C_1-C_6)$-alkyl or, $NH_2$;
or R5 is phenyl, 1- or 2-naphthyl, biphenyl or a heterocyclic radical, where the rings or ring systems may be substituted up to two times by F, Cl, Br, I, CN, OH, $O(C_1-C_8)$-alkyl, $O(C_3-C_8)$-cycloalkyl, O—CO—$(C_1-C_8)$-alkyl, O—CO—$(C_3-C_8)$-cycloalkyl, $S(O)_{0-2}(C_1-C_8)$-alkyl, $S(O)_{0-2}(C_3-C_8)$-cycloalkyl, $NH_2$, NH—$(C_1-C_8)$-alkyl, NH—$(C_3-C_8)$-cycloalkyl, $N[(C_1-C_8)$-alkyl$]_2$, $N[(C_3-C_8)$-cycloalkyl$]_2$, NH—CO—$(C_2-C_8)$-alkyl, NH—CO—$(C_3-C_8)$-cycloalkyl; $SO_3H$, $SO_2$—$NH_2$, $SO_2$—NH—$(C_1-C_8)$-alkyl, $SO_2$—NH—$(C_3-C_8)$-cycloalkyl; NH—$SO_2$—$NH_2$, NH—$SO_2$—$(C_1-C_8)$-alkyl, NH—$SO_2$—$(C_3-C_8)$-cycloalkyl, O—$CH_2$—COOH, O—$CH_2$—CO—$O(C_1-C_8)$-alkyl, COOH, CO—$O(C_1-C_8)$-alkyl, CO—O—$(C_3-C_8)$-cycloalkyl, CO—$NH_2$, CO—NH$(C_1-C_8)$-alkyl, CO—N$[(C_1-C_8)$-alkyl$]_2$, $(C_1-C_8)$-alkyl, or $(C_3-C_8)$-cycloalkyl, wherein, on the alkyl groups, in each case, one to seven hydrogen atoms may be replaced by fluorine;
R9 is F, Cl, Br, CN, $CF_3$, $(C_1-C_{18})$-alkyl, $(C_3-C_4)$-cycloalkyl, or $(C_6-C_8)$-cycloalkyl, wherein, on the alkyl groups, one to seven hydrogen atoms may be replaced by fluorine;
or R9 is $(CH_2)_u$-aryl or $(CH_2)_u$-heteroaryl, where u is 0 to 6 and aryl may be phenyl, 1- or 2-napthyl, biphenyl or a heterocyclic radical, where the rings or ring systems of aryl, heteroaryl, or the heterocyclic radical may be substituted up to two times by F, Cl, Br, I, CN, OH, $O(C_1-C_8)$-alkyl, $O(C_3-C_8)$-cycloalkyl, O—CO—$(C_1-C_8)$-alkyl, O—CO—$(C_3-C_8)$-cycloalkyl, $S(O)_{0-2}(C_1-C_8)$-alkyl, $S(O)_{0-2}(C_3-C_8)$-cycloalkyl, $NH_2$, NH—$(C_1-C_8)$-alkyl, NH—$(C_3-C_8)$-cycloalkyl, $N[(C_1-C_8)$-alkyl$]_2$, $N[(C_3-C_8)$-cycloalkyl$]_2$, NH—CO—$(C_2-C_8)$-alkyl, NH—CO—$(C_3-C_8)$-cycloalkyl; $SO_3H$, $SO_2$—$NH_2$, $SO_2$—NH—$(C_1-C_8)$-alkyl, $SO_2$—NH—$(C_3-C_8)$-cycloalkyl; NH—$SO_2$—$NH_2$, NH—$SO_2$—$(C_1-C_8)$-alkyl, NH—$SO_2$—$(C_3-C_8)$-cycloalkyl, O—$CH_2$—COOH, O—$CH_2$—CO—$O(C_1-C_8)$-alkyl, COOH, CO—$O(C_1-C_8)$-alkyl, CO—O—$(C_3-C_8)$-cycloalkyl, CO—$NH_2$, CO—NH$(C_1-C_8)$-alkyl, CO—N$[(C_1-C_8)$-alkyl$]_2$, $(C_1-C_8)$-alkyl, or $(C_3-C_8)$-cycloalkyl, wherein, on the alkyl groups, in each case, one to seven hydrogen atoms may be replaced by fluorine;
and their physiologically acceptable salts;
provided that when R1, R2, R3 and R4 are all hydrogen, and X—Y—R5 is S-phenyl, then R9 is other than phenyl; and that when R1, R2, R3 and R4 are all hydrogen, and X—Y—R5 is —S-benzyl-4-carboxy, then R9 is other than methyl.

3. A compound according to claim 1 of the formula I wherein
R1, R2, R3, R4 independently of one another are H, F, Cl, Br, CN; $N_3$, $NO_2$, OH, $O(C_1-C_8)$-alkyl, $O(C_3-C_8)$-cycloalkyl, O—$CH_2$-phenyl, O-phenyl, O—CO—$(C_1-C_8)$-alkyl, O—CO—$(C_3-C_8)$-cycloalkyl, $NH_2$, NH—$(C_1-C_8)$-alkyl, $N[(C_1-C_8)$-alkyl$]_2$, COOH, CO—$O(C_1-C_8)$-alkyl, $(C_1-C_8)$-alkyl, $(C_3-C_8)$-cycloalkyl, $(C_2-C_8)$-alkenyl, $(C_2-C_8)$-alkynyl, wherein on the alkyl, alkenyl and alkynyl groups, in each case, one to seven hydrogen atoms may be replaced by fluorine,
or an aryl radical wherein the aryl radical is phenyl,
or heterocycle wherein heterocycle is 1-imidazolyl;
where the aryl radical or heterocycle may be substituted up to two times by F, Cl, Br, CN, OH, $(C_1-C_4)$-alkyl, $CF_3$, or O—$(C_1-C_4)$-alkyl, and wherein, on the alkyl groups, one to seven hydrogen atoms may be replaced by fluorine;
X is S, $SO_2$;
Y is $(CH_2)_p$, where p may be 0 or 1;
R5 is $CF_3$, or $(C_1-C_8)$-alkyl, wherein, on, the alkyl groups, one to seven hydrogen atoms may be replaced by fluorine;
or R5 is phenyl, pyridinyl, where the rings of the phenyl and pyridinyl may be substituted up to two times by F, Cl, Br, or $(C_1-C_8)$-alkyl;
R9 is F, Cl, Br, $(C_1-C_8)$-alkyl, wherein, on, the alkyl groups, one to seven hydrogen atoms may be replaced by fluorine;
or R9 is $(CH_2)_u$-phenyl, where phenyl may be substituted up to two times by F, Cl, Br, $(C_1-C_8)$-alkyl;
and their physiologically acceptable salts;
provided that when R1, R2, R3 and R4 are all hydrogen, and X—Y—R5 is S-phenyl, then R9 is other than phenyl; and that when R1, R2, R3 and R4 are all hydrogen, and X—Y—R5 is —S-benzyl-4-carboxy, then R9 is other than methyl.

4. A pharmaceutical composition comprising a pharmaceutically effective amount of a compound according to claim 1 and a pharmaceutically acceptable carrier.

5. A process for the preparation of the compounds of formula I as claimed in claim 1 wherein, (1) X is S and R9 is not hydrogen, comprising, (a) (i) reacting the compound of formula II

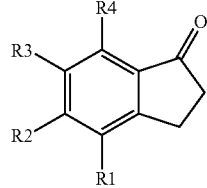

with a fluorinating agent, (ii) reacting the compound of formula II with an alkylating agent, or (iii) condensing the compound of formula II with an aldehyde and then reducing the condensation product, to form a compound of formula IV

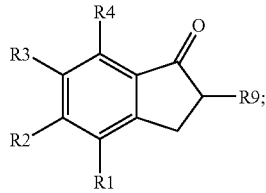

(b) brominating the compound of formula IV and then reacting the bromination product with a metal salt of H—X—Y—R5;

(2) X is SO and R9 is not hydrogen, comprising oxidizing selectively the compound of formula I wherein X is S;

(3) X is $SO_2$ and R9 is not hydrogen, comprising, oxidizing the compound of formula I wherein X is S and R9 is not hydrogen, or oxidizing the compound of formula I wherein X is SO, and R9 is not hydrogen; or X is SO or $SO_2$ and wherein Y is a bond and R9 is hydrogen, comprising, converting the compound of formula II wherein R9 is hydrogen according to the scheme below,

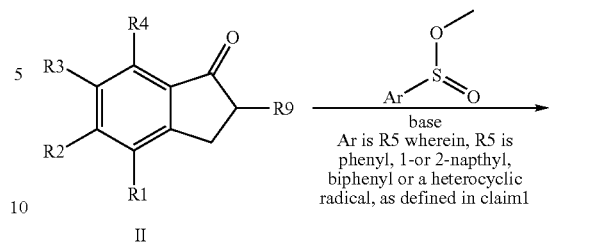

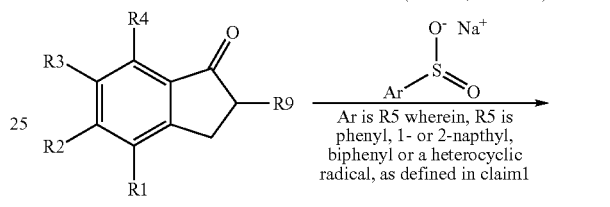

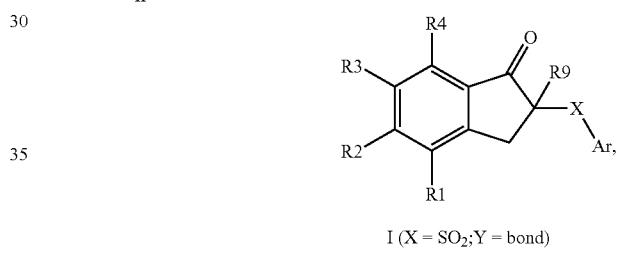

further comprising converting the resulting compounds of formula I wherein X is $SO_2$ and R9 is hydrogen to form compounds of formula I wherein X is $SO_2$ and R9 is not hydrogen.

* * * * *